United States Patent [19]

Warriner

[11] Plant 4,541

[45] Jun. 10, 1980

[54] ROSE PLANT

[75] Inventor: William A. Warriner, Tustin, Calif.

[73] Assignee: Jackson & Perkins Co., Medford, Oreg.

[21] Appl. No.: 960,489

[22] Filed: Nov. 13, 1978

[51] Int. Cl.[2] ..... A01H 5/00

[52] U.S. Cl. ..... Plt./19

[58] Field of Search ..... Plt./18, 19

*Primary Examiner*—Robert E. Bagwill
*Assistant Examiner*—James R. Feyrer
*Attorney, Agent, or Firm*—Klarquist, Sparkman, Campbell, Leigh, Hall & Whinston

[57] ABSTRACT

A well branched, plant of the hybrid tea class with large, leathery foliage, and blooms becoming Neyron Rose, having very little fragrance.

5 Drawing Figures

BACKGROUND OF THE INVENTION

The present invention relates to a new and distinct variety of rose plant of the hybrid tea class which was originated by me by crossing an unnamed hybrid tea variety with pollen of the variety Medallion, U.S. Plant Pat. No. 2,997.

The primary objective of this breeding was to produce a new variety of the hybrid tea class with well-formed blooms of a medium pink color carried on a well branched, upright plant. This objective was fully achieved as evidenced by the following unique combination of characteristics which are outstanding in this new variety and which distinquish it from its parents as well as from all other varieties of which I am aware:

1. A well branched plant of typical hybrid tea habit.
2. Large, leathery foliage.
3. Buds of near Brick red when very tight, becoming Neyron Rose in open stages.
4. Very double, well imbricated blooms of 40 to 50 petals.
5. A slight fragrance.

Asexual reproduction of this new cultivar by budding as performed at Wasco, Calif., shows that the foregoing characteristics and distinctions come true to form and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with Wilson's Horticultural Color Chart, except where ordinary dictionary significance of color is indicated.

Parentage:
- *Seed parent.*—Unnamed variety.
- *Pollen parent.*—Medallion.

Classification:
- *Botanical.*—Rosa hybrid.
- *Commercial.*—Hybrid tea.

FLOWER

Observations made from specimens grown at Irvine, Calif., in August of 1978.

Blooming habit: Continuous.

Bud:
- *Size.*—1 to 1¼ inches when petals start to unfurl.
- *Form.*—Pointed ovoid, broad base.
- *Color.*—When sepals first divide, near Brick Red (016) turning, as sepals fall and before petals unfold, to Delft Rose (020); when half blown, upper side of petals near Neyron Rose (623); lower side of petals, near Neyron Rose (623/1).
- *Sepals.*—Color: Outer surface Scheeles Green (860) overlaid with Garnet Brown (00918/3); inner surface Scheeles Green (860/2) with light amount of tomentum. Three sepals lightly appendaged. Two unappendaged sepals, hairy edged.
- *Receptacle.*—Color: Scheeles Green (860). Shape: Funnel. Size: Large, broad. Surface: Nearly smooth; has a few stipitate glands near base.
- *Peduncle.*—Length: Short. Surface: Prickly. Color: Bronzy. Strength: Stiff, erect.
- *Opening.*—Petals curl outward without quilling. Outer petals tend to remain perpendicular to stem.

Bloom:
- *Size.*—Large. Average open size 4½ inches.
- *Borne.*—Singly or several together.
- *Stems.*—Medium, strong.
- *Form.*—When first open, high centered. Permanence: Retains its form to the end.
- *Petalage.*—Number of petals under normal conditions: 40 to 50.
- *Color.*—Center of flower: Upper side of petals: Near Neyron Rose (623). Reverse side of petals: Near Neyron Rose (623/1). Base of petals: Small area near Amber Yellow (505/1). General tonality from a distance: Neyron Rose (623).
- *Variegations.*—None.
- *Discoloration.*—Tonality at end of first day, Neyron Rose (623); third day, Neyron Rose (623/1).
- *Fragrance.*—Slight.

Petals:
- *Texture.*—Thick.
- *Shape.*—Round.
- *Form.*—Tips slightly recurved.
- *Arrangement.*—Imbricated. Petaloids in center, few.
- *Persistence.*—Drop off cleanly.
- *Lastingness.*—On the plant, long. As cut flower, long.

Reproductive parts:

*Stamens, anthers.*—Medium. Color, yellow. Arrangement, regular around styles.

*Filaments.*—Color: Light yellow.

*Pollen.*—Lemon yellow.

*Styles.*—Color: Mostly light yellow, pink near stigmas.

*Stigmas.*—Color: Yellow.

PLANT

Form: Bush.

Growth: Vigorous, upright, branching at an angle of about 10 degrees.

Foliage: Number of leaflets on normal mid-stem leaves 5.

*Size.*—Large.

*Quantity.*—Normal.

*Color.*—New foliage: Garnet Brown (00918/3). Old foliage: Slightly darker than Spinach Green (0960).

Leaflets:

*Shape.*—Broadly elliptic and pointed.

*Texture.*—Leathery upper side.

*Edge.*—Serrated.

*Serration.*—Single, small.

*Petiole.*—Rachis: Color, reddish. Underside, prickles.

*Stipules.*—Long, bearded.

*Disease resistance.*—Normally resistant to mildew under normal growing conditions at Irvine, Calif.

Wood:

*New wood.*—Color: Dark green. Bark: Smooth.

*Old wood.*—Color: Green. Bark: Smooth.

Prickles:

*Quantity.*—On main stalks from base, ordinary to few. On laterals from stalk, few.

*Form.*—Long, oval base, hooked downward.

*Color when young.*—Brown.

*Position.*—Irregular.

Small prickles:

*Quantity.*—On main stalks, few. On laterals, few.

*Color.*—Brown.

I claim:

1. A new and distinct variety of rose plant of the hybrid tea class, substantially as herein shown and described, characterized particularly as to novelty by the unique combination of its well-branched plant, large foliage, very double, slightly fragrant flower of Neyron Rose.

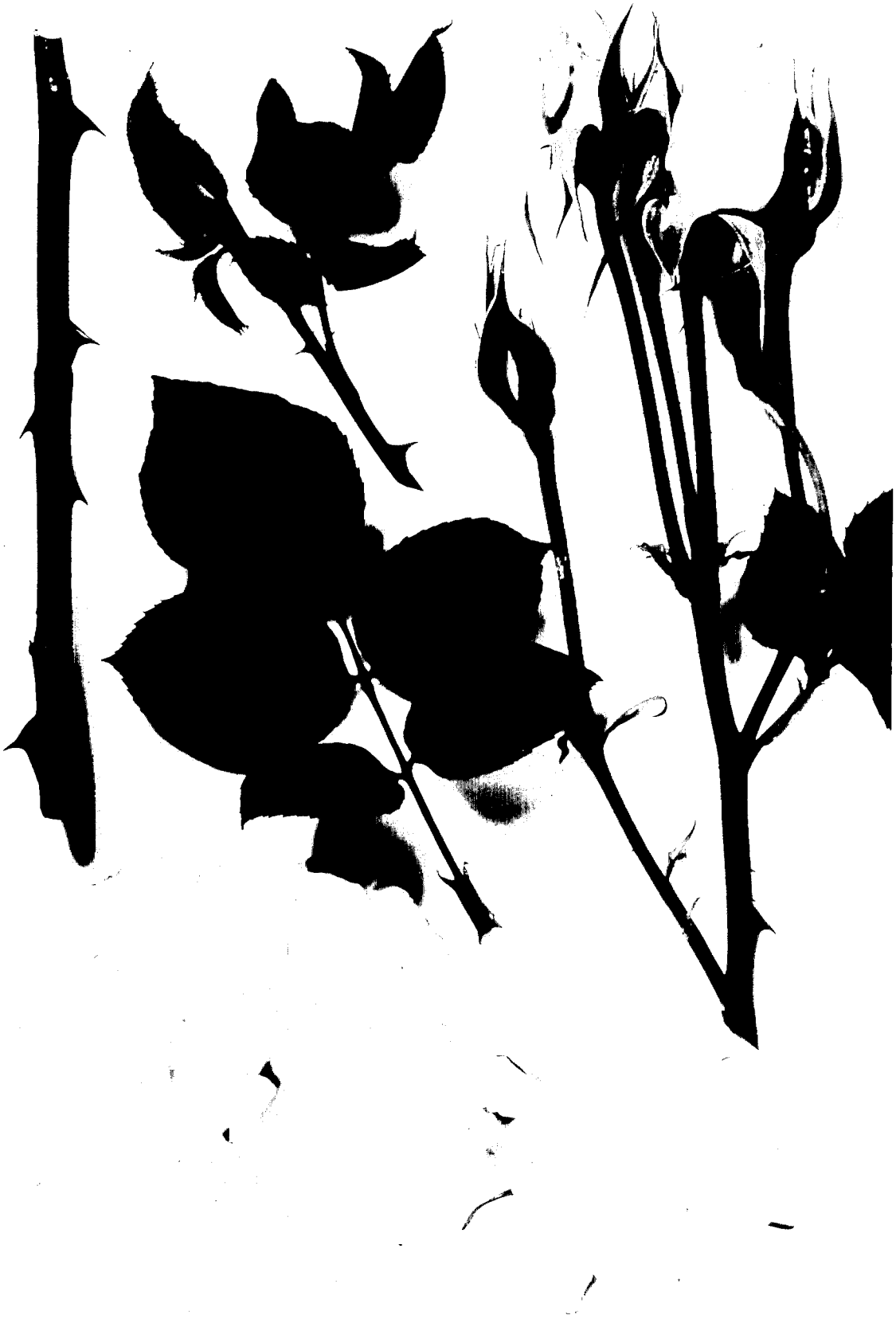

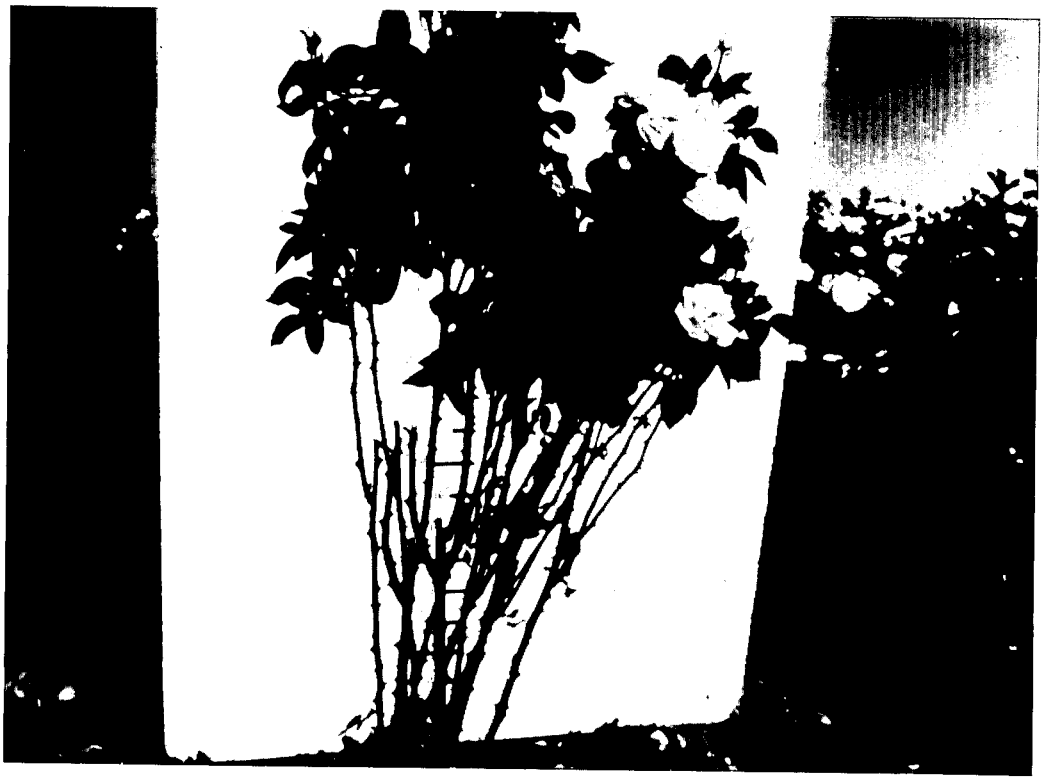

* * * * *